United States Patent
Schramm

(10) Patent No.: US 7,063,672 B2
(45) Date of Patent: Jun. 20, 2006

(54) INTEGRATED BIOPSY NEEDLE ASSEMBLY

(75) Inventor: John B. Schramm, Skokie, IL (US)

(73) Assignee: Inter-V Manan, Wheeling, IL (US)

( * ) Notice: Subject to any disclaimer, the term of this patent is extended or adjusted under 35 U.S.C. 154(b) by 430 days.

(21) Appl. No.: 10/356,008

(22) Filed: Jan. 31, 2003

(65) Prior Publication Data

US 2004/0153002 A1  Aug. 5, 2004

(51) Int. Cl.
A61B 10/00 (2006.01)

(52) U.S. Cl. .................................................... 600/564

(58) Field of Classification Search ........ 600/564–567, 600/562; 604/157–159, 164.11, 171; 606/167, 606/170
See application file for complete search history.

(56) References Cited

U.S. PATENT DOCUMENTS

| | | |
|---|---|---|
| 2,623,521 A | 12/1952 | Shaw |
| 2,705,949 A | 4/1955 | Silverman |
| 2,710,000 A | 6/1955 | Cromer et al. |
| 3,477,423 A | 11/1969 | Griffith |
| 3,629,912 A | 12/1971 | Klopp |
| 3,989,033 A | 11/1976 | Halpern et al. |
| 4,282,884 A | 8/1981 | Boebel |
| 4,326,519 A | 4/1982 | D'Alo et al. |
| 4,396,021 A | 8/1983 | Baumgartner |
| 4,461,305 A | 7/1984 | Cibley |
| 4,519,392 A | 5/1985 | Lingua |
| 4,600,014 A | 7/1986 | Beraha |
| 4,667,684 A | 5/1987 | Leigh |
| 4,699,154 A | 10/1987 | Lindgren |
| 4,702,261 A | 10/1987 | Cornell et al. |
| 4,716,886 A | 1/1988 | Schulman et al. |
| 4,732,215 A | 3/1988 | Hopper |
| 4,766,907 A | 8/1988 | De Groot et al. |
| 4,776,346 A | 10/1988 | Beraha et al. |
| 4,881,551 A | 11/1989 | Taylor |
| 4,890,626 A | 1/1990 | Wang |
| 4,893,635 A | 1/1990 | De Groot et al. |
| 4,907,599 A | 3/1990 | Taylor |
| 4,917,100 A | 4/1990 | Nottke |
| 4,940,061 A | 7/1990 | Terwilliger et al. |
| 4,953,558 A | 9/1990 | Akerfeldt |
| 4,958,625 A * | 9/1990 | Bates et al. .................. 600/567 |
| 4,976,269 A | 12/1990 | Mehl |
| 4,991,600 A | 2/1991 | Taylor |
| 5,005,585 A | 4/1991 | Mazza |

(Continued)

FOREIGN PATENT DOCUMENTS

DE  20 36 725  2/1971

(Continued)

Primary Examiner—Max F. Hindenburg
Assistant Examiner—Brian Szmal
(74) Attorney, Agent, or Firm—Greenberg Traurig

(57) ABSTRACT

An integrated biopsy needle assembly for use with a conventional biopsy gun comprises a hollow cannula, a stylet, a cannula hub operatively fixed to the proximal end of the cannula, a stylet hub operatively fixed to the proximal end of the stylet, and a hub strap operably associated therewith. The cannula hub is operatively fixed to the hub strap, while the stylet hub is capable of movement relative to the hub strap. The hub strap includes a top member, at least one side wall and at least one bottom member, thereby forming an inner channel. The cannula and stylet hubs further include a base and a cap, with the cannula and stylet hub caps being maintained at all times within the inner channel of the hub strap.

14 Claims, 5 Drawing Sheets

U.S. PATENT DOCUMENTS

| | | |
|---|---|---|
| 5,025,797 A | 6/1991 | Baran |
| 5,027,797 A | 7/1991 | Bullard |
| 5,036,860 A | 8/1991 | Leigh et al. |
| 5,048,538 A | 9/1991 | Terwilliger et al. |
| 5,090,419 A | 2/1992 | Palestrant |
| 5,092,870 A | 3/1992 | Mittermeier |
| 5,121,751 A * | 6/1992 | Panalletta ................ 600/567 |
| 5,125,413 A | 6/1992 | Baran |
| 5,146,921 A | 9/1992 | Terwilliger et al. |
| 5,156,160 A | 10/1992 | Bennett |
| 5,161,542 A * | 11/1992 | Palestrant ................ 600/567 |
| 5,172,702 A | 12/1992 | Leigh et al. |
| 5,183,054 A | 2/1993 | Burkholder et al. |
| 5,188,118 A | 2/1993 | Terwilliger |
| 5,195,533 A | 3/1993 | Chin et al. |
| 5,213,110 A | 5/1993 | Kedem et al. |
| 5,224,470 A | 7/1993 | Schnepp-Pesch et al. |
| 5,236,334 A | 8/1993 | Bennett |
| 5,243,994 A * | 9/1993 | Ranalletta ................ 600/567 |
| 5,249,582 A | 10/1993 | Taylor |
| 5,282,476 A | 2/1994 | Terwilliger |
| 5,284,156 A | 2/1994 | Schramm et al. |
| 5,306,260 A | 4/1994 | Kanner |
| 5,316,013 A | 5/1994 | Striebel, II et al. |
| 5,335,672 A | 8/1994 | Bennett |
| 5,353,804 A | 10/1994 | Kornberg et al. |
| 5,368,045 A * | 11/1994 | Clement et al. ............ 600/567 |
| 5,388,589 A | 2/1995 | Davis |
| 5,415,182 A * | 5/1995 | Chin et al. ................ 600/567 |
| 5,433,725 A | 7/1995 | Christian et al. |
| 5,476,101 A | 12/1995 | Schramm et al. |
| 5,492,130 A | 2/1996 | Chiou |
| 5,507,298 A | 4/1996 | Schramm et al. |
| D369,858 S | 5/1996 | Baker et al. |
| 5,535,755 A | 7/1996 | Heske |
| 5,538,010 A | 7/1996 | Darr et al. |
| 5,546,957 A | 8/1996 | Heske |
| 5,551,442 A | 9/1996 | Kanner et al. |
| 5,560,373 A | 10/1996 | De Santis |
| 5,564,436 A | 10/1996 | Hakky et al. |
| 5,570,699 A | 11/1996 | Kass |
| 5,617,874 A | 4/1997 | Baran |
| 5,752,923 A * | 5/1998 | Terwilliger ................ 600/562 |
| 5,779,647 A | 7/1998 | Chau et al. |
| 5,788,651 A | 8/1998 | Weilandt |
| 5,842,999 A | 12/1998 | Pruitt et al. |
| 5,876,354 A * | 3/1999 | Quinn et al. ................ 600/562 |
| 5,944,673 A | 8/1999 | Gregoire et al. |
| 5,951,489 A | 9/1999 | Bauer |
| 5,989,196 A | 11/1999 | Chu et al. |
| 5,989,197 A | 11/1999 | Avaltroni |
| 5,993,399 A | 11/1999 | Pruitt et al. |
| 6,007,497 A | 12/1999 | Huitema |
| 6,050,955 A | 4/2000 | Bryan et al. |
| 6,083,176 A | 7/2000 | Terwilliger |
| 6,110,129 A * | 8/2000 | Terwilliger ................ 600/567 |
| 6,120,463 A | 9/2000 | Bauer |
| 6,126,617 A | 10/2000 | Weilandt et al. |
| 6,142,955 A | 11/2000 | Farascioni et al. |
| 6,193,673 B1 | 2/2001 | Viola et al. |
| 6,196,978 B1 | 3/2001 | Weilandt et al. |
| 6,221,030 B1 | 4/2001 | Avaltroni |
| 6,261,241 B1 | 7/2001 | Burbank et al. |
| 6,273,861 B1 | 8/2001 | Bates et al. |
| 6,322,523 B1 | 11/2001 | Weilandt et al. |
| 6,328,701 B1 * | 12/2001 | Terwilliger ................ 600/567 |
| 6,358,217 B1 | 3/2002 | Bourassa |
| 6,436,054 B1 | 8/2002 | Viola et al. |
| 6,488,636 B1 | 12/2002 | Bryan et al. |
| 2001/0007925 A1 | 7/2001 | Richart et al. |
| 2003/0225343 A1* | 12/2003 | Miller et al. ................ 600/567 |
| 2004/0158172 A1* | 8/2004 | Hancock .................... 600/564 |

FOREIGN PATENT DOCUMENTS

| | | |
|---|---|---|
| EP | 0 868 882 A2 | 10/1997 |
| WO | WO 87/06815 | 11/1987 |
| WO | WO 91/01112 | 7/1990 |
| WO | WO 91/07915 | 7/1991 |

* cited by examiner

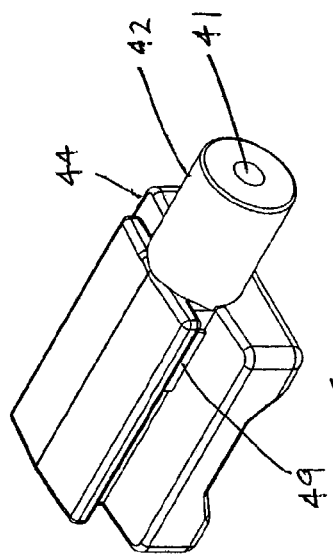
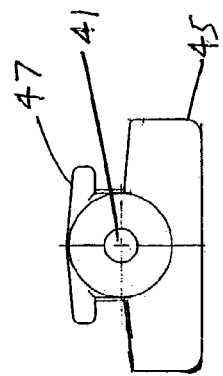
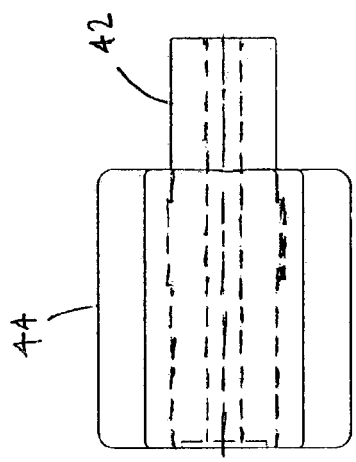
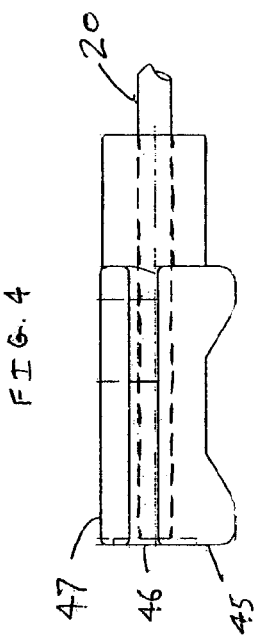
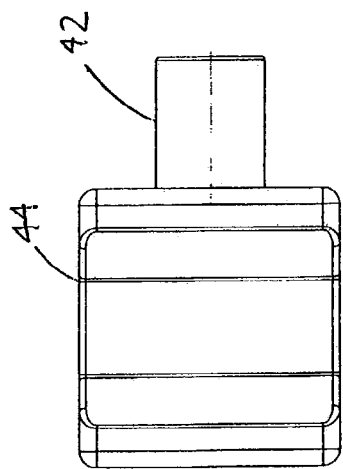
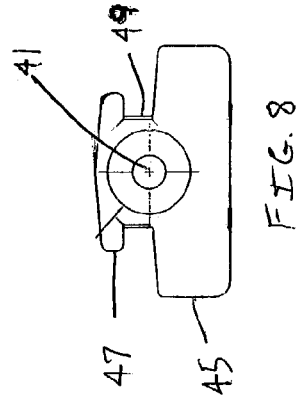
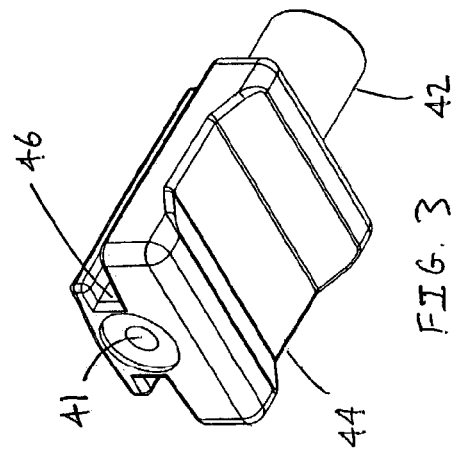

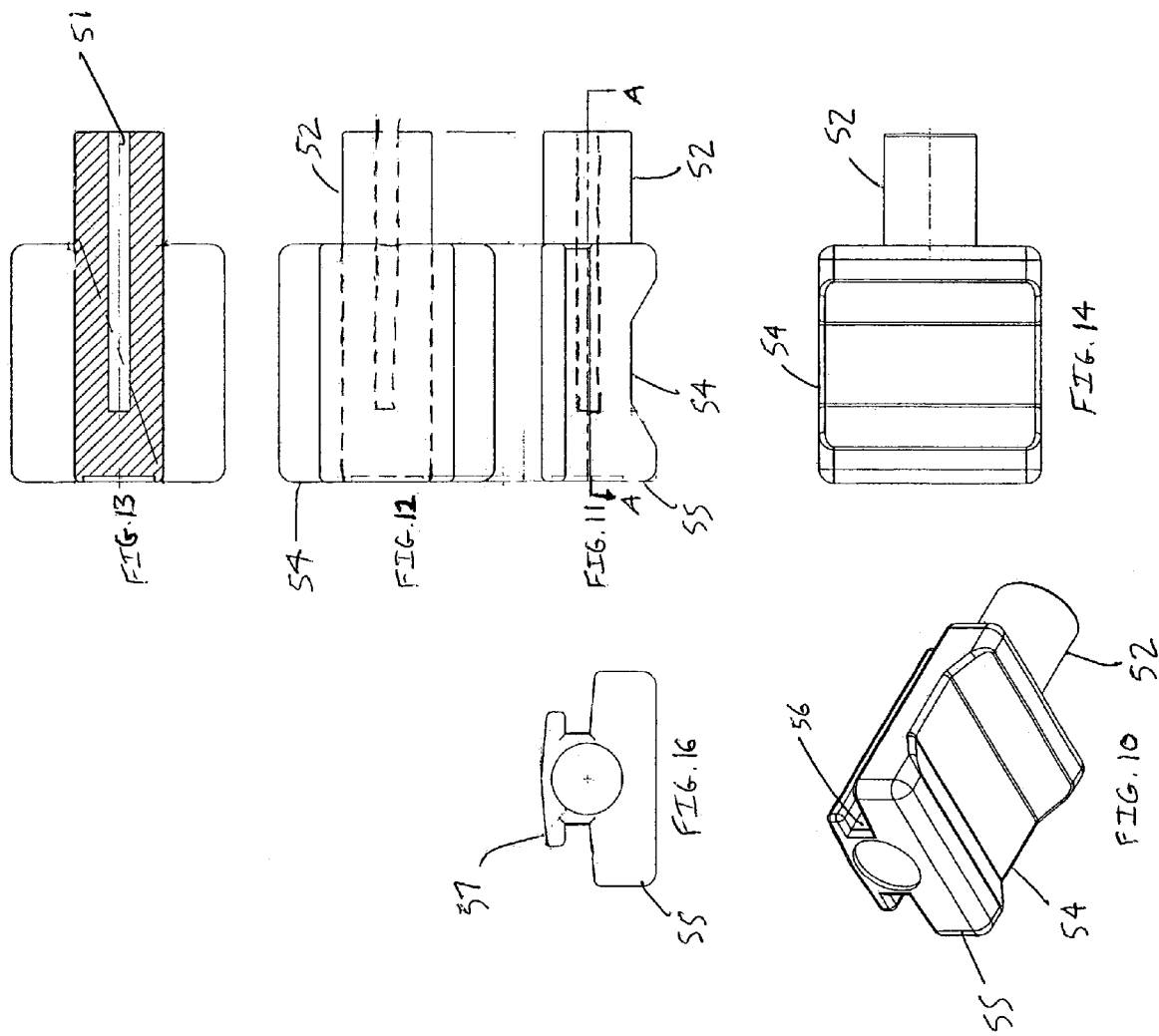

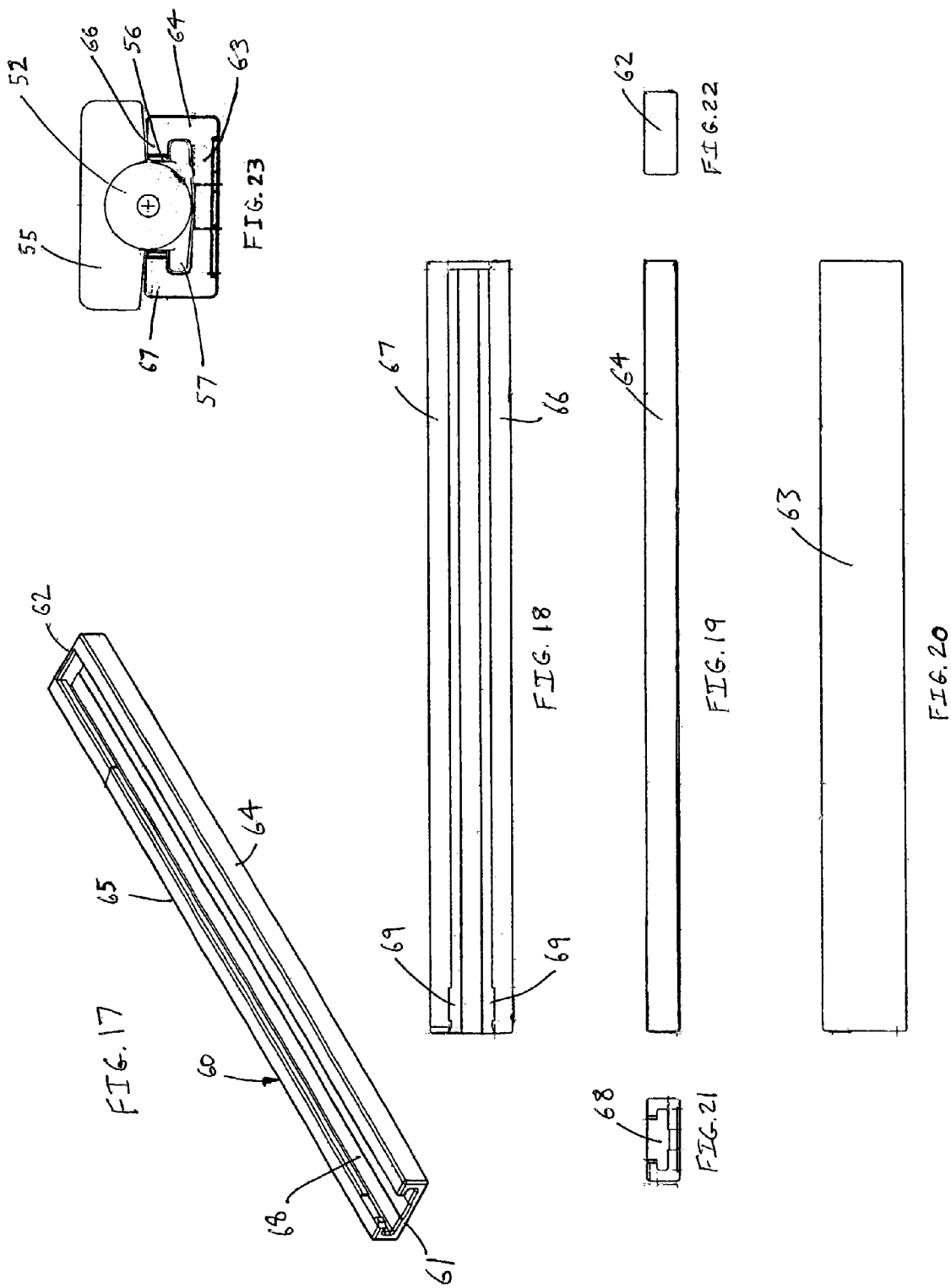

INTEGRATED BIOPSY NEEDLE ASSEMBLY

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not applicable.

BACKGROUND OF THE DISCLOSURE

1. Field of the Invention

The present invention is directed to biopsy needle assemblies for use with biopsy gun devices known in the prior art and, more specifically, to an integrated biopsy needle assembly capable of being readily inserted within and removed from such devices.

2. Background Art

Various devices for obtaining tissue samples from a living being are previously known in the art. One such device is known as a "biopsy gun", which typically includes an outer cannula and inner stylet that are "fired" in sequence in order to obtain and sever a sample of tissue. One such previously-known device is disclosed in Schramm et al., U.S. Pat. No. 5,476,101. The device disclosed by Schramm et al. utilizes a separate cannula and stylet, each having sharpened distal ends for penetrating tissue, as is well known in the art. The proximal ends of the cannula and the stylet are operably fixed to respective hubs, which are adapted to be retained in corresponding yokes contained within the biopsy gun. The stylet also includes a hollowed-out tissue sampling recess near the distal end thereof. The separate cannula and stylet are joined, prior to use, by inserting the stylet within the hollow cannula. Once so joined, the needle assembly can then be inserted into the biopsy gun, by inserting the cannula and stylet hubs within the corresponding yokes, which serve to maintain the position of the cannula and stylet relative to one another during use of the device.

In order to obtain a tissue sample, the biopsy gun must first be "cocked" to prepare it for use, as disclosed in Schramm et al. Once the gun has been cocked, the distal ends of the cannula and stylet are then inserted into the tissue region from which a sample is desired. After the distal ends of the cannula and stylet are placed at the desired location, the gun is then "fired", causing the yoke associated with the stylet to be easily propelled forward, thereby exposing the tissue sampling recess associated with the stylet, and causing a tissue sample to prolapse into the recess. Next, the yoke associated with the cannula is propelled forward in rapid succession, so that the cannula once again covers the tissue sampling recess on the stylet, thereby causing the sharpened distal end of the cannula to sever the tissue sample contained within the tissue sampling recess. The tissue sample may then be retrieved by first removing the distal ends of the cannula and stylet from the tissue, then removing the cannula and stylet assembly from the biopsy gun, and finally retracting the cannula relative to the stylet in order to expose the tissue sampling recess.

Biopsy gun devices such as those disclosed by Schramm et al. require that separate cannula and stylet elements be joined prior to use, with the respective hub elements then being inserted into the corresponding yokes within the biopsy gun. This use of a separate cannula and stylet adds an additional assembly step to the biopsy process. Also, after the tissue sample is taken and the needle assembly has been removed from the biopsy gun, the user must take extra care to ensure that the stylet does not accidentally slide out of the cannula, thereby affecting the tissue sample.

These concerns were previously addressed by Terwilliger, U.S. Pat. No. 6,110,129, and Terwilliger, U.S. Pat. No. 6,328,701, which disclosed a biopsy needle for use in a biopsy gun, comprising a conventional cannula and stylet, and having a guiding needle holder including an integrated spacer, and first and second connecting elements. The first connecting element holds the proximal end of the cannula and is displaceably attached along the length of the integrated spacer. The second connecting element holds the proximal end of the stylet and is fixedly attached to the proximal end of the integrated spacer. The connecting elements each have an opening that facilitates insertion of the biopsy needle into a conventional biopsy gun. The integrated design ensures that the cannula and stylet are joined and properly oriented relative to each other prior to use, without the need for the user to manually insert the stylet into the cannula thereby facilitating the insertion of the needle assembly into the biopsy gun.

The needle assembly disclosed by the Terwilliger patents presents certain disadvantages of its own. Namely, the Terwilliger design, in which the stylet is operatively fixed to the integrated spacer, requires that the biopsy gun propel both the stylet and the integrated spacer when the stylet tip is first fired into the tissue to be sampled. As a result, a greater force may be required to be exerted on the stylet than would be required if the stylet were capable of moving relative to the integrated spacer. As a result, the biopsy gun must include a propelling means (typically, a spring) capable of providing sufficient force to accelerate both the stylet and the integrated spacer to the desired velocity. Additionally, the Terwilliger design can affect the retrieval of tissue samples from the stylet tissue sampling recess, due to the fact that the first connecting element is seated completely within the integrated spacer. As a result, it may be difficult for the user to manipulate the first connecting element, after the needle assembly has been removed from the biopsy gun, in order to retract the cannula from the stylet to expose the tissue sampling recess, and to remove the tissue sample therefrom.

It is therefore an object of the present invention to provide an integrated biopsy needle assembly for use with a conventional biopsy gun, in which the stylet is capable of movement relative to the spacer element, so as to minimize the amount of force needed to initially propel the stylet tip into the tissue to be sampled.

It is a further object of the present invention to provide a biopsy needle assembly in which retrieval of the tissue sample from the tissue sampling recess on the stylet is facilitated, by providing cannula and/or stylet hubs which are readily manipulable—so as to facilitate movement of the cannula and stylet relative to one another after the needle assembly has been removed from the biopsy gun.

SUMMARY OF THE INVENTION

The invention comprises an integrated biopsy needle including a cannula having distal and proximal ends and a hollow cross-section therebetween, a stylet having distal and proximal ends and adapted for sliding movement within the cannula, a cannula hub operatively fixed to the proximal end of the cannula, a stylet hub operatively fixed to the proximal end of the stylet, and a hub strap operably associated with the cannula hub and the stylet hub. The cannula hub is operatively fixed to the hub strap, while the stylet hub is oriented so as to be movable relative to the hub strap. The hub strap further includes a top member, at least one side wall and at least one bottom member, thereby forming an inner channel.

Additionally, the cannula hub and stylet hub each include a base and a cap, which are retained within the inner channel of the hub strap. Further, at least one of the cannula hub base and the stylet hub base has a width at least equal to, or greater than, the width of the hub strap.

In a further embodiment of the invention, the cannula hub includes at least one outward projection, and the hub strap further includes at least one notch associated with one of the top member, the at least one side wall and the at least one bottom member. The at least one outward projection is retained within the at least one notch, thereby preventing movement of the cannula hub relative to the hub strap. The hub strap further includes at least one end wall to restrain the movement of the stylet hub within the inner channel.

In addition, the stylet further includes a tissue sampling recess proximate the distal end thereof. The distal ends of the stylet and cannula may be sharpened so as to facilitate the penetration of tissue.

The cannula hub, stylet hub and hub strap may also be constructed from a plastic material.

BRIEF DESCRIPTION OF THE DRAWINGS

FIG. 2 is a top front perspective view of the cannula hub of the integrated biopsy needle assembly of FIG. 1A.

FIG. 3 is a bottom rear perspective view of the cannula hub of the integrated biopsy needle assembly of FIG. 1A.

FIG. 4 is a top plan view of the cannula hub of the integrated biopsy needle assembly of FIG. 1A.

FIG. 5 is a bottom plan view of the cannula hub of the integrated biopsy needle assembly of FIG. 1A.

FIG. 6 is a side elevational view of the cannula hub of the integrated biopsy needle assembly of FIG. 1A.

FIG. 7 is a front elevational view of the cannula hub of the integrated biopsy needle assembly of FIG. 1A.

FIG. 8 is a rear elevational view of the cannula hub of the integrated biopsy needle assembly of FIG. 1A.

FIG. 9 is a top front perspective view of the stylet hub of the integrated biopsy needle assembly of FIG. 1A.

FIG. 10 is a bottom rear perspective view of the stylet hub of the integrated biopsy needle assembly of FIG. 1A.

FIG. 11 is a side elevational view of the stylet hub of the integrated biopsy needle assembly of FIG. 1A.

FIG. 12 is a top plan view of the stylet hub of the integrated biopsy needle assembly of FIG. 1A.

FIG. 13 is a sectional view of the stylet hub of the integrated biopsy needle assembly of FIG. 1A, taken along the lines A—A of FIG. 11.

FIG. 14 is a bottom plan view of the stylet hub of the integrated biopsy needle assembly of FIG. 1A.

FIG. 15 is a front elevational view of the stylet hub of the integrated biopsy needle assembly of FIG. 1A.

FIG. 16 is a rear elevational view of the stylet hub of the integrated biopsy needle assembly of FIG. 1A.

FIG. 17 is a bottom front perspective view of the hub strap of the integrated biopsy needle assembly of FIG. 1A.

FIG. 18 is a bottom plan view of the hub strap of the integrated biopsy needle assembly of FIG. 1A.

FIG. 19 is a side elevational view of the hub strap of the integrated biopsy needle assembly of FIG. 1A.

FIG. 20 is a top plan view of the hub strap of the integrated biopsy needle assembly of FIG. 1A.

FIG. 21 is a front elevational view of the hub strap of the integrated biopsy needle assembly of FIG. 1A.

FIG. 22 is a rear elevational view of the hub strap of the integrated biopsy needle assembly of FIG. 1A.

FIG. 23 is an end view of the hub strap and stylet hub of the integrated biopsy needle assembly of FIG. 1A, looking in the direction of the proximal end of the hub strap, in which the cannula hub is omitted.

DETAILED DESCRIPTION OF THE DRAWINGS

Figure 1A:
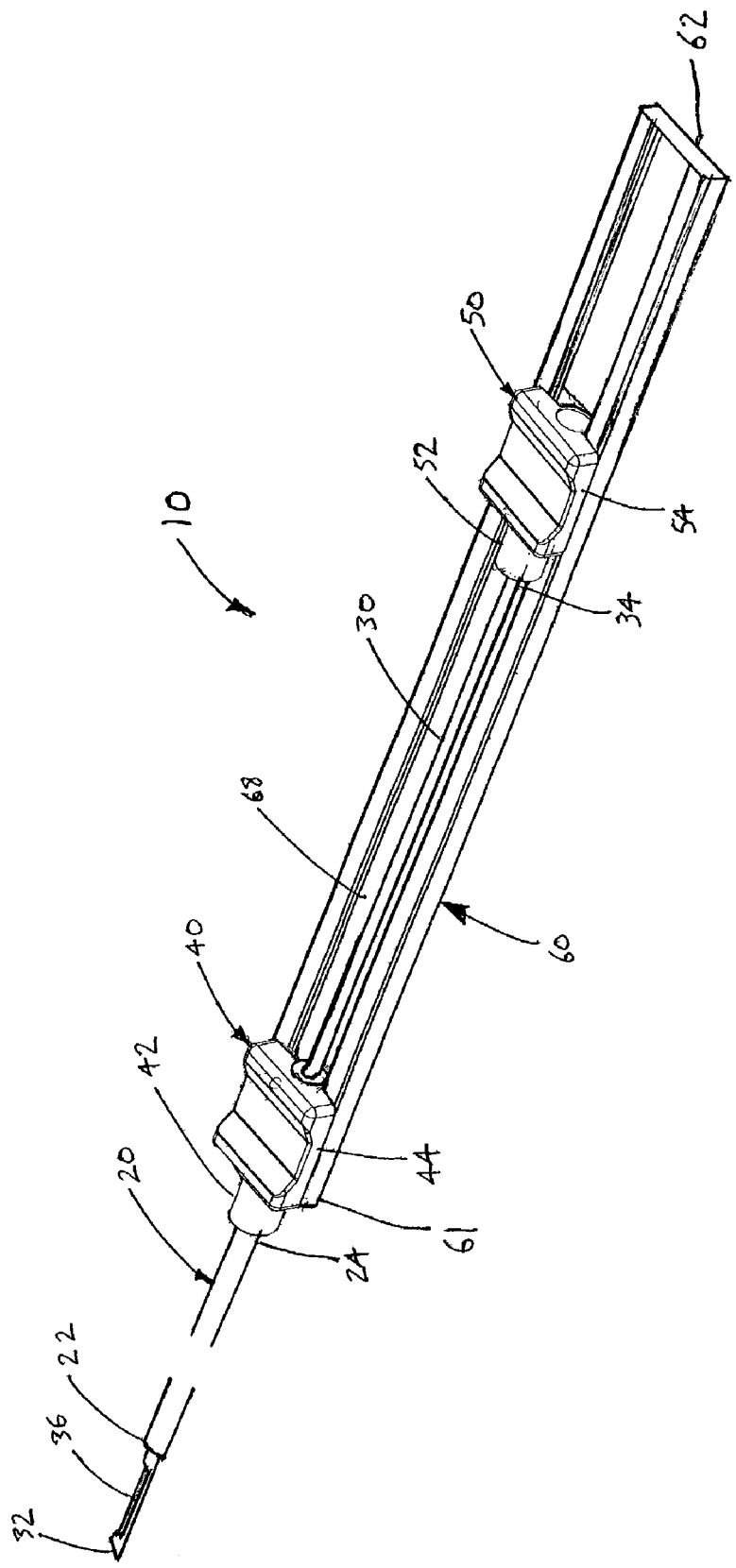
FIG. 1A is a bottom rear perspective view of the integrated biopsy needle assembly of the present invention, in which the slidable stylet hub is shown in a forward orientation, thereby causing the tissue sampling recess on the stylet to be exposed.

While this invention is susceptible of embodiment in many different forms, there is shown in the drawings, and will be described in detail herein, one specific embodiment, with the understanding that the present embodiment is to be considered as an exemplification of the principles of the invention and is not intended to limit the invention to the embodiments illustrated.

Figure 1B:
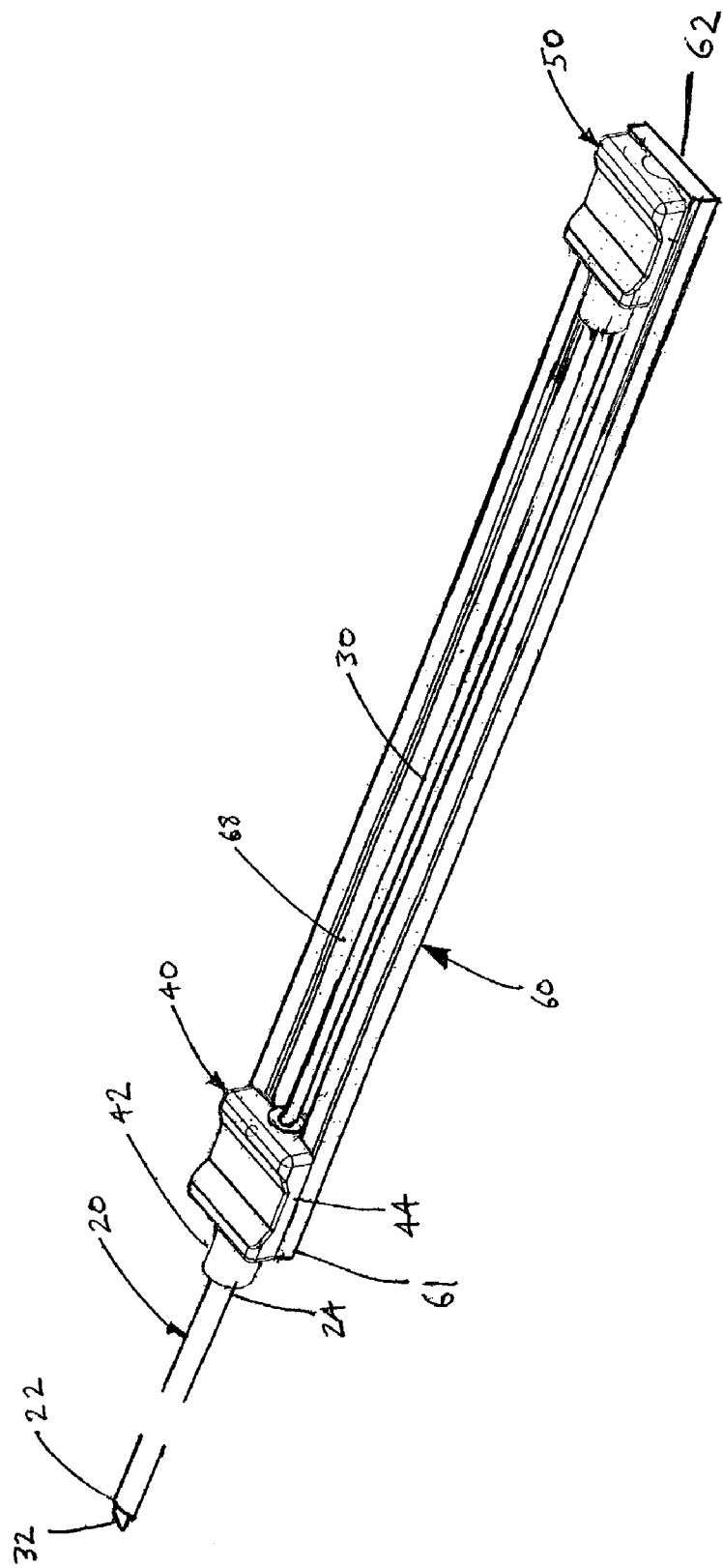
FIG. 1B is a bottom rear perspective view of the integrated biopsy needle assembly of FIG. 1A, in which the slidable stylet hub is shown in a rearward orientation, thereby causing the tissue sampling recess on the stylet to be covered by the cannula.

The present invention is directed to an integrated biopsy needle assembly 10, for obtaining tissue samples from a desired region of tissue. Needle assembly 10 is intended to be used in a conventional biopsy gun device known in the art, such as that disclosed in Schramm et al., U.S. Pat. No. 5,476,101. Needle assembly 10 is shown generally in FIGS. 1A and 1B as comprising cannula 20, stylet 30, cannula hub 40, stylet hub 50 and hub strap 60. Cannula 20 comprises a hollow, round needle, as is well known in the art of biopsy instruments, having sharpened distal end 22 and proximal end 24. Likewise, stylet 30 comprises a solid round needle, as known in the art, having sharpened distal end 32 and proximal end 34. Stylet 30 is slidably received within cannula 20, such that cannula 20 and stylet 30 are operationally coupled to one another at all times during use of biopsy needle assembly 10. Stylet 30 also includes tissue sampling recess 36 adjacent distal end 32, as known in the art, which comprises a notch in stylet 30 adapted to receive a tissue sample when needle assembly 10 is "fired", or sequentially activated, by a biopsy gun, as is further described below.

Cannula hub 40, shown in FIGS. 2–8, comprises bore 41, forward barrel portion 42 and rear body portion 44. Proximal end 24 of cannula 20 is seated within barrel portion 42, such that cannula 20 is fixedly attached to cannula hub 40. Bore 41, which extends completely through forward barrel portion 42 and rear barrel portion 44, permits stylet 30 is permitted to slide freely through cannula hub 40 and cannula 20. Rear body portion 44 of cannula hub 40 further comprises base 45, stem 46, cap 47 and projections 49 located on opposite sides of stem 46. Similarly, stylet hub 50, shown in FIGS. 9–16, comprises partial bore 51, forward barrel portion 52 and rear body portion 54, with rear body portion 54 further comprising base 55, stem 56 and cap 57. Proximal end 34 of stylet 30 is seated within partial bore 51, as a result of which stylet 30 is fixedly attached to stylet hub 50. Cannula hub 40, stylet hub 50 and hub strap 60 are preferably constructed from a lightweight plastic, although other materials may be used as desired.

Cannula hub base 45 and stylet hub base 55 are shaped so as to securably fit into correspondingly-shaped recesses (not shown) located on the first and second yokes, respectively, of a conventional biopsy gun, such as that disclosed in Schramm et al., U.S. Pat. No. 5,476,101. This permits cannula 20 and stylet 30 to be sequentially "fired" forward by the first and second yokes, respectively, upon actuation of the biopsy gun—as described in more detail hereinbelow. In addition to their facilitating the placement of needle assembly 10 into a biopsy gun, cannula hub base 45 and stylet hub base 55 also serve to facilitate the manipulation of stylet 30 and cannula 20 by the user when needle assembly 10 is not inserted within a biopsy gun. Specifically, and in contrast to the prior art devices discussed above, cannula hub base 45 and stylet hub base 55 extend outward beyond the bottom of inner channel 68, in order to provide a structure for the user to readily grasp while manipulating cannula hub 40 and stylet hub 50 to retrieve a tissue sample. Additionally, stylet hub base 55 is preferably slightly wider than hub strap 60, as can be seen from FIG. 23, so as to be more readily graspable by the user. As a result, the user can move stylet 30 relative to cannula 20 by simply pushing or pulling on stylet hub base 55 with one hand, while grasping hub strap 60 with the other hand.

Hub strap 60, shown in FIGS. 17–22, comprises distal end 61, proximal end wall 62, top member 63, side walls 64 and 65, bottom members 66 and 67 and inner channel 68. The design of hub strap 60 ensures that caps 47 and 57 of cannula hub 40 and stylet hub 50, respectively, are retained within inner channel 68 at all times, thereby operatively coupling cannula 20 and stylet 30 to hub strap 60. This configuration is more clearly shown in FIG. 23, which demonstrates how cap 57 of movable stylet hub 50 is constrained in place within inner channel 68 of hub strap 60 by bottom members 66 and 67. Specifically, cap 57 is wider than the gap between bottom members 66 and 67, as a result of which cap 57 is not able to be removed from inner channel 68.

Bottom members 66 and 67 further include notches 69 adjacent the distal ends thereof. Additionally, cannula hub cap 47 is positioned within inner channel 68, such that projections 49 are seated within notches 69 on bottom members 66 and 67. As a result, cannula hub 40 is restrained from moving relative to hub strap 60, and therefore remains operatively fixed to hub strap 60 at all times during operation of needle assembly 10. Furthermore, other means of fixing cannula hub 40 in place relative to hub strap 60 are contemplated, for example, placement of projections on hub strap 60 which interact with corresponding notches or holes on cannula hub 40, use of a pin element extending through both cannula hub 40 and hub strap 60, or any other desired structure.

Similarly, stylet hub cap 57 is positioned within inner channel 68 between cap 47 of stylet hub 40 and proximal end wall 62. Unlike cannula hub cap 47, however, stylet hub cap 57 is not fixed in place relative to hub strap 60. Rather, stylet hub 50 is movable relative to hub strap 60, between positions defined by proximal end wall 62 and cannula hub 40. This configuration permits stylet 30 to slide within cannula 20, while maintaining stylet 30 and cannula 20 is a permanently integrated relationship with one another.

In order to obtain a tissue sample from a patient, integrated biopsy needle assembly 10 is first inserted into a conventional biopsy gun, such as that disclosed by Schramm et al., U.S. Pat. No. 5,476,101, such that cannula hub base 45 and stylet hub base 55 are seated within corresponding recesses located on the first and second yokes (not shown), respectively, of the biopsy gun. The biopsy gun is then cocked prior to use, thereby placing needle assembly 10 into the orientation of FIG. 1B, in which movable stylet hub 50 is at its maximum distance from fixed stylet hub 40, and nearly all of stylet 30, including tissue sampling recess 36, is contained within cannula 20, with only the sharpened distal tip 32 of stylet 30 exposed. Next, cannula 20 and stylet 30 are inserted at the desired location within the tissue to be sampled, with joined distal ends 22 and 32 serving to penetrate the tissue, as well known in the art. The biopsy gun is then fired, causing stylet 30 to be propelled rapidly forward relative to cannula 20, thereby causing needle assembly 10 to be placed into a configuration similar to that shown in FIG. 1A, in which tissue sampling recess 36 is exposed. This forward movement of stylet 40 will cause a sample of tissue at the desired location to prolapse within tissue sampling recess 36. Next, cannula 20 (along with hub strap 60) is propelled forward in rapid succession, causing sharpened distal end 22 of cannula 20 to sever the tissue sample contained within tissue sampling recess 36 from the surrounding tissue. Once the desired tissue sample has been safely isolated within tissue sampling recess 36, cannula 20 and stylet 30 are jointly removed from the tissue. Finally, biopsy needle assembly 10 is then removed from the biopsy gun to permit retrieval of the tissue sample from tissue sampling recess 36. To do so, the user may simply grasp base 55 in order to push stylet hub 50 forward, relative to hub strap 60, to expose tissue sampling recess 36, and then remove the tissue sample therefrom.

The integrated needle assembly of the present invention represents a significant improvement over the prior art Terwilliger needle assembly, in that upon firing of the biopsy gun, only stylet 30 and stylet hub 50 are propelled forward. Notably, unlike in the device disclosed by Terwilliger, hub strap 60 is not propelled forward upon initial firing of the biopsy gun. As a result, less force is required to be exerted on the stylet in order to effect the initial penetration of stylet 30 into the tissue region from which a sample is desired to be taken. As a result, the biopsy gun can utilize a smaller spring to propel the stylet yoke, thereby resulting in both weight and cost savings. Moreover, the risk of injury to doctor or patient associated with accidental firing of the biopsy gun is lessened, due to the reduction in propulsion force being exerted on the stylet.

Additionally, while in the preferred embodiment cannula hub 40 is operatively fixed to hub strap 60, the present invention also contemplates an alternate embodiment, in which both cannula hub 40 and stylet hub 50 are capable of movement relative to hub strap 60, if such an arrangement is desired. Such an embodiment could be effected merely by removing projections 49 from cannula hub 40, thereby permitting cannula hub 40 to slide within inner channel 68. Further, an additional embodiment of the invention is contemplated in which cannula 20 is fixed directly to hub strap 60 itself, rather than to a separate cannula hub element.

The foregoing description and drawings merely explain and illustrate the invention, and the invention is not limited thereto except insofar as the pending claims are so limited, as those skilled in the art and having the present disclosure before them will be able to make modifications and variations therein without departing from the scope of the invention.

What is claimed is:

1. An integrated biopsy needle assembly comprising:
   a cannula having a distal end and a proximal end, and a hollow cross-section therebetween;
   a stylet having a distal end and a proximal end, the stylet being adapted for sliding movement within the cannula;
   a cannula hub operatively fixed to the proximal end of the cannula;
   a stylet hub operatively fixed to the proximal end of the stylet; and
   a hub strap operably associated with the cannula hub and the stylet hub, the cannula and stylet sharing a common longitudinal axis, in which at least a portion of said stylet reciprocates telescopically within at least a portion of said cannula, wherein the cannula hub is restrainably fixed to the hub strap to preclude longitudinal movement of both the cannula and the cannula hub relative thereto and the stylet hub, and, in turn, the stylet, is configured to be longitudinally movable relative to the hub strap.

2. The biopsy needle assembly of claim 1, wherein the hub strap comprises a top member, at least one side wall and at least one bottom member, thereby forming an inner channel.

3. The biopsy needle assembly of claim 2, wherein the cannula hub and the stylet hub each comprise a base and a cap.

4. The biopsy needle assembly of claim 3, wherein the cannula hub cap and the stylet hub cap are retained within the inner channel of the hub strap.

5. The biopsy needle assembly of claim 3, wherein at least one of the cannula hub base and the stylet hub base has a width at least equal to the width of the hub strap.

6. The biopsy needle assembly of claim 2, wherein the cannula hub further comprises at least one outward projection.

7. The biopsy needle assembly of claim 6, wherein the hub strap further comprises at least one notch associated with one of the top member, the at least one side wall and the at least one bottom member.

8. The biopsy needle assembly of claim 7, wherein the at least one outward projection is retained within the at least one notch, thereby preventing movement of the cannula hub relative to the hub strap.

9. The biopsy needle assembly of claim 2, wherein the hub strap further includes at least one end wall to restrain the movement of the stylet hub within the inner channel.

10. The biopsy needle assembly of claim 1, wherein the stylet further comprises a tissue sampling recess proximate the distal end thereof.

11. The biopsy needle assembly of claim 1, in which the distal end of the stylet is sharpened so as to facilitate penetration of tissue.

12. The biopsy needle assembly of claim 1, in which the distal end of the cannula is sharpened so as to facilitate penetration of tissue.

13. The biopsy needle assembly of claim 1, in which the cannula hub, stylet hub and hub strap are constructed from a plastic material.

14. An integrated biopsy needle assembly comprising:
   a cannula having a distal end and a proximal end, and a hollow cross-sectional therebetween;
   a stylet having a distal end and a proximal end, the stylet being adapted for sliding movement within the cannula;
   a cannula hub operatively fixed to the proximal end of the cannula;
   a stylet hub operatively fixed to the proximal end of the stylet; and
   a hub strap operably associated with the cannula hub and the stylet hub, wherein the cannula hub is operatively fixed to the hub strap and the stylet hub is oriented so as to be movable relative to the hub strap;
   wherein the hub strap comprises a top member, at least one side wall and at least one bottom member, thereby forming an inner channel;
   wherein the cannula hub and the stylet hub each comprise a base and a cap; and
   wherein at least one of the cannula hub base and the stylet hub base has a width greater than the width of the hub strap.

* * * * *